United States Patent [19]

Birr et al.

[11] 4,353,821

[45] Oct. 12, 1982

[54] METHOD OF PREPARING THYMOSIN $\alpha_1$ AND DERIVATIVES THEREOF

[75] Inventors: Christian Birr, Leimen-St. Ilgen; Ulrich Stollenwerk, Heidelberg, both of Fed. Rep. of Germany

[73] Assignee: Max Planck-Gesellschaft zur Forderung der Wissenschaften E.V., Gottingen, Fed. Rep. of Germany

[21] Appl. No.: 133,031

[22] Filed: Mar. 24, 1980

[30] Foreign Application Priority Data

May 15, 1979 [DE] Fed. Rep. of Germany ....... 2919592

[51] Int. Cl.³ ............................................. C07C 103/52
[52] U.S. Cl. ............................................. 260/112.5 R
[58] Field of Search .................. 260/112.5 R; 424/177

[56] References Cited
U.S. PATENT DOCUMENTS 4,079,127 3/1978 Goldstein et al. ............ 260/112.5 R
4,148,788 4/1979 Wang .................................. 424/177

OTHER PUBLICATIONS

I. Z. Siemion, et al., "Peptides", Proceedings of the Fifteenth European Peptide Symposium 1978.
Merrifield, Peptides (1978), 19 & 248–251.
Birr, et al., Angew Chem. Int. Ed. Engl. 18, (1979) 394;5.

*Primary Examiner*—Delbert R. Phillips
*Attorney, Agent, or Firm*—Felfe & Lynch

[57] ABSTRACT

Polypeptides of the sequence Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn, wherein at least one of the amino acids 10, 15, 21, 25 and/or 28 is present as amide or alkyl amide, and/or amino acid 1 bears an acyl group other than acetyl, having up to 6 carbon atoms, especially an acyl glycine residue. In addition, certain thymosin $\alpha_1$ fragments I to VII are provided.

8 Claims, 1 Drawing Figure

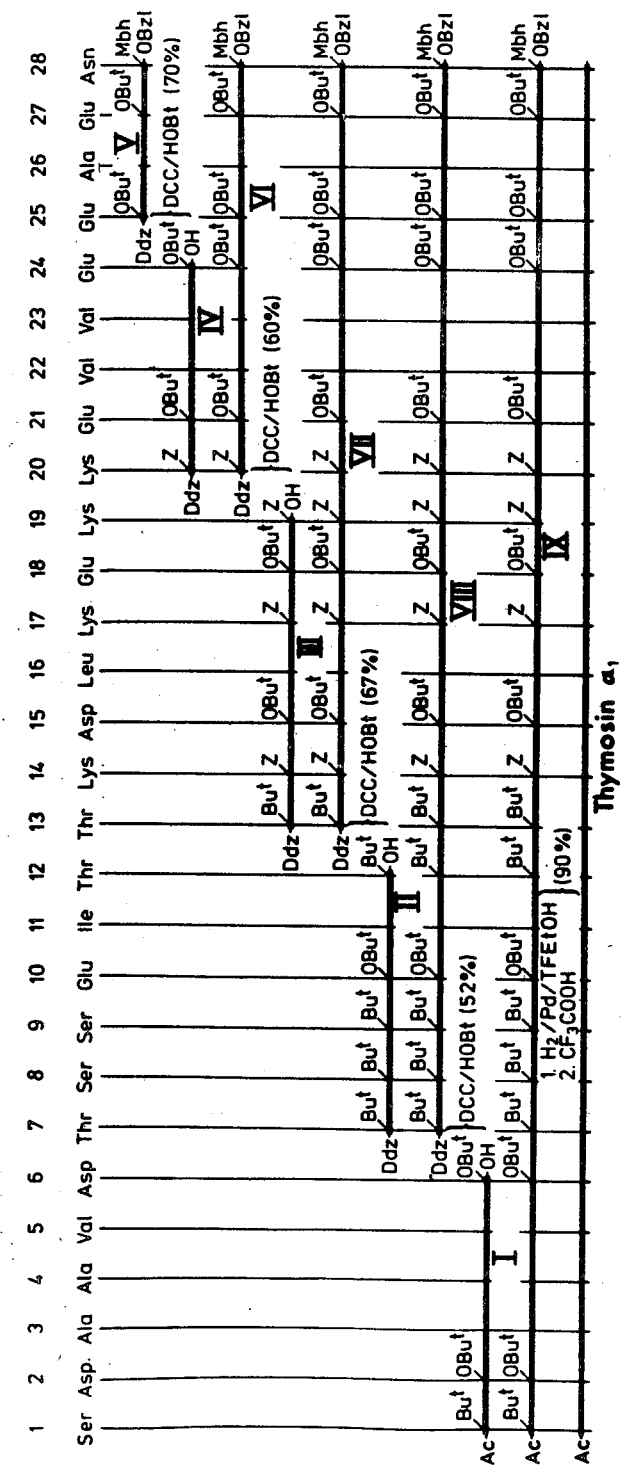

METHOD OF PREPARING THYMOSIN $\alpha_1$ AND DERIVATIVES THEREOF

DESCRIPTION

The invention relates to a method of preparing thymosin $\alpha_1$ and certain derivatives thereof from peptide fragments.

Thymosin $\alpha_1$ is an especially acid polypeptide of the thymus gland, which has the sequence Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn, and in which the number 1 amino acid, serine, is acetylated. Interesting biological properties have been found in thymosin $\alpha_1$ which suggest that it might be useful in combatting cancer and in the regulation of the immunological defense mechanism (Cancer Treatment Reports, Vol. 62, No. 11 (1978)). For example, it has been found that the immunosuppression resulting from irradiation in cancer therapy can be reduced by treatment with thymosin $\alpha_1$.

There is therefore an interest in finding a method for the synthetic preparation of thymosin $\alpha_1$.

The full chemical synthesis of thymosin $\alpha_1$ is already disclosed in J.A.C.S. 101, 1, 253–254 (1979). In this process, several different peptide fragments are synthesized by the hitherto conventional methods of peptide synthesis, and then these peptide fragments are condensed with one another by various methods, particularly the azide method. The known process, however, has the disadvantage of being very difficult, while nevertheless producing only very low yields.

The invention is addressed to the problem of creating a method for the synthesis of thymosin $\alpha_1$, which will not have these disadvantages and will arrive at the desired product with a good yield by a simple reaction. The method is furthermore to be suitable without great modification for the production of biologically interesting derivatives and analogs of thymosin $\alpha_1$.

This problem is solved in accordance with the invention by a method for the preparation of thymosin $\alpha_1$ or a derivative thereof, in which at least one of the amino acids 10, 15, 21, 25 and 28 is in the form of amide or alkyl amide, and/or the acetyl group is replaced by another acyl group, by preparing a series of peptide fragments containing protective groups, condensing them, and then splitting off the protective groups, which is characterized in that (a) the N-terminally unprotected, C-terminally esterified or carrier-bound C-terminal peptide fragment is condensed, in an at least 1.5 times less than stoichiometric amount, with the adjacent N-terminally protected, C-terminally unprotected peptide fragment, in an anhydrous organic solvent containing dicyclohexylcarbodiimide and 1-hydroxybenzotriazole, (b) The Ddz group of the condensed fragment is split off by the addition of trifluoroacetic acid in a slight stoichiometric excess, (c) excess acid is neutralized with an organic base, and (d) the N-terminally unprotected, lengthened C-terminal fragment thus obtained is condensed with the next N-terminally Ddz-protected fragment by steps (a), (b) and (c) repeatedly until the peptide chain is complete, and finally the remaining protective groups are split off in a conventional manner, using as lateral protective groups t-butyl ester groups for Asp and Glu, tertbutyl groups for Ser and Thr, benzyloxycarbonyl groups for Lys, and 4,4'-dimethoxybenzohydryl groups for Asn, and, if desired, replacing the N-terminal acetyl group with a different acyl group.

The abbreviations used herein correspond to the proposals of the IUPAG-IUB (J. Biol. Chem. 247, 977–983 (1972)). Ddz represents $\alpha,\alpha$-dimethyl-3,5-dimethoxybenzyloxycarbonyl, Z represents benzyloxycarbonyl, Ac represents acetyl, OBut represents t-butyl ester and MbH represents 4,4'-dimethyloxybenzohydryl. The alkyl groups are straight-chain or branched residues having 1 to 6, preferably 1 to 4 carbon atoms. The carriers are the carrier materials known to the technical expert to be suitable for the immobilization of peptides and proteins.

In the method of the invention it is essential to use the fragments which represent the N-terminal end of the thymosin $\alpha_1$ molecule in an excess of at least 1.5 times, and preferably 2 to 2.5 times the stoichiometric amount. Since in the condensation of two fragments a new, larger C-terminal fragment having an N-terminal Ddz protective group is formed, and the latter can be split off with a very small amount of acid for the next condensation step, only a small amount of base is required for neutralization. The great number of individual steps and intervening purifications that were commonly used in the methods known heretofore are thus simplified by the fact that only a single chromatographic separation of the reaction mixture in a column serves for the isolation of each reaction product. It is preferred to use Sephadex LH20 in the solvent, methanol and 2,2,2-trifluoroethanol. In the case of carrier-bound fragment condensation, even the last-mentioned chromatographic intermediate isolation of the product is unnecessary.

Since in accordance with the invention the process is performed in an anhydrous organic solvent, no special drying steps for the removal of water are required. Also, the purification of the fully protected end product, which is best performed by chromatography, can be accomplished in the same anhydrous organic solvent.

Dimethyl formamide is used preferentially as the solvent for step (a). Other suitable solvents are N-methylpyrrolidone and mixtures of the two, as well as dimethylacetamide.

Dichloromethane is preferred as the solvent in step (b). Other suitable solvents are chloroform, tetrahydrofuran and dioxane.

It is especially preferred to use a solution of 1% to about 5% trifluoroacetic acid in dichloromethane. A special advantage of trifluoroacetic acid is that it can also be used in conjunction with the final splitting off of the tertbutyl ester protective groups and of the 4,4'-dimethoxybenzohydryl protective group, merely by increasing its concentration.

For the neutralization, basically any organic tertiary amines which are soluble in the organic solvent or are carrier-bound can be used. N-methylmorpholine is especially preferred, because it suppresses racemization and thereby improves the optical purity of the product.

After step (a) is completed, the solvent is best withdrawn in vacuo, and the residue is purified by chromatography, for example through a molecular sieve material such as cross-linked dextran, polystyrene or the like. The chromatography is performed in a suitable anhydrous solvent, such as an alkanol, a halogenated hydrocarbon, or the like. Methanol is preferred. In the case of carrier-bound fragment condensation, the polymeric carrier is simply washed with dimethylformamide and dichloromethane.

The peptide fragments used as starting products for the process of the invention can be prepared by the known methods of peptide synthesis. Their synthesis is preferably performed also with the use of Ddz protective groups, mixed anhydrides of the Ddz-amino acids with isobutyloxycarbonyl chloride and N-methylmorpholine being built up by a step-by-step lengthening at the N-terminus. It is especially preferred to dissolve 1.5 to 2 equivalents of the particular Ddz-amino acid, N-methylmorpholine and secbutyloxycarbonyl chloride in dichloromethane and mix this solution at about $-10°$ to $-20°$ C. with a solution obtained by the reaction of one equivalent of Ddz-aminoacid-tertbutylester or of Ddz-oligopeptide-tertbutylester in dichloromethane containing 1 to 5% of trifluoroacetic acid and keeping it at standard temperature for one-quarter to half an hour and then neutralizing with N-methylmorpholine. The mixed solutions are then allowed to react at room temperature for about 30 minutes to 2 hours. The reaction mixture that is obtained is concentrated in vacuo until dry and purified chromatographically through an appropriate chromatographic material such as a cross-linked dextran such as Sephadex LH20, in a solvent such as methanol. After the removal of this solvent, the next condensation step can be performed immediately in the described manner until the particular peptide fragment has been prepared. In the case of carrier-bound fragment condensation, the polymeric carrier is washed with dimethyl formamide and dichloromethane after the reaction has taken place.

The building up of thymosin $\alpha_1$ from the fragments thus obtained is further represented in the appended drawing. It can be seen that five fragments are prepared, which consist of the amino acids 1 to 6 (fragment I), 7 to 12 (fragment II), 13 to 19 (fragment III), 20 to 24 (fragment IV) and 25 to 28 (fragment V). Fragment V, as the C-terminal fragment, is then, in accordance with the invention, reacted with fragment IV, thereby obtaining the lengthened C-terminal fragment VI. In the same manner, fragment VI is again reacted with fragment III, fragment VII then developing as the new C-terminal fragment. This last is reacted with fragment II to form fragment VIII, and this is finally reacted with fragment I to form the finished peptide chain IX from which the protective group is split off. If in a given case the acetyl group is to be replaced by a different acyl group, this is done in the preparation of fragment I. Fragments I and V are prepared preferably as benzyl esters, V being carrier-bound if desired, and II, III and IV as methyl esters. The release of the carboxyl end group from the ester is accomplished best by alkaline saponification, in aqueous dioxane in the case of the methyl ester, and in a mixture of tetrahydrofuran and methanol in the case of the benzyl ester.

The condensation reaction itself is performed preferably in dimethyl formamide as solvent. The yields in the individual condensation steps are excellent and amount to as much as 90%. In the case of fragment I, it is desirable to remove the benzyl ester group by hydrogenation. A suitable solvent is a mixture of propanol and glacial acetic acid, as well as 2,2,2-trifluoroethanol. It is desirable to use palladium on charcoal, or palladium black or platinum black.

As previously mentioned, the method of the invention also permits the synthesis of certain derivatives of thymosin $\alpha_1$, namely those in which the amino acids 10 (Glu), 15 (Asp), 21 (Glu) and 28 (Asn) have an amide or alkyl amide group instead of a carboxyl group. In this case, in the corresponding step of the synthesis of the fragment, instead of the amino acid present in the natural thymosin $\alpha_1$, the derivatives of this amino acid which have been transformed to the amide or alkyl amide are used. In the case of Asn, the corresponding diamide is used, since Asn is already an amide.

These derivatives are of special therapeutic interest, and have a different action from that of thymosin $\alpha_1$. As new compounds, these analogs are also subject matter of the invention.

Also, the N-terminal acetyl group can be replaced with another acyl group to vary the effect or the strength of the effect. In this case an acyl glycine residue is introduced instead of the acetyl residue.

The following example, in conjunction with the appended drawing, will further explain the invention.

Preparation of Thymosin $\alpha_1$

Fragments I (1 to 6), II (7 to 12), III (13 to 19), IV (20 to 24) and V (25 to 28) were constructed in solution, with the use of excess mixed anhydrides of the Ddz amino acids with isobutyloxycarbonyl chloride and N-methyl morpholine, by N-terminal, step-by-step sequential prolongation, with protection on all sides. After that, fragments I and V were in the form of benzyl esters and II, III and IV in the form of methyl esters, with the following yields calculated through all steps: I (67%), II (20%), III (31%), IV (56%) and V (39%).

After alkaline saponification in aqueous dioxane, fragment IV was condensed with V in dimethyl formamide, after the Ddz group had first been split off from the latter with 1% trifluoroacetic acid in dichloromethane (V/V). The condensation was performed with a mixture of dicyclohexylcarbodiimide and 1-hydroxybenzotriazole (DCC/HOBt) in 24 hours at 20° C. with a 70% yield. Fragment VI is thus obtained.

After alkaline saponification in an aqueous solution of tetrahydrofuran and methanol, fragment III is attached to fragment VI under the conditions described above, in dimethyl formamide at room temperature in 66 hours. Fragment VII is thus obtained with a 60% yield.

In the next step, after the Ddz has been split off in the same manner as in the case of fragment V, fragment VII is attached to fragment II at the N-terminus after this fragment has first been saponified in an 8:2 mixture (V/V) of dioxane and water. The condensation was performed for 18 hours at 0° C. and for 10 hours at 20° C. The yield was 67% of fragment VIII.

Prior to the final condensation, the benzyl ester group was split off from the N-terminal acetyl fragment I by hydrogenolysis in a mixture of propanol and glacial acetic acid. The free acid of fragment I was reacted for 24 hours with fragment VIII in a 2:1 mixture (V/V) of N-methylpyrrolidone and dimethylformamide, after the Ddz had been split off. The yield was 52% of product IX.

Product IX was purified in 2,2,2-trifluorethanol by chromatography through Sephadex LH20. Analysis of the amino acids (calculated values between parentheses; 6 N HCl 110° C., 24 hours): Asp 4.11 (4); Thr 2.64 (3); Ser 2.38 (3); Glu 6.80 (6); Lys 4.59 (4); Ile 1.13 (1); Leu 1.23 (1); Ala 2.51 (3); Val 2.41 (3).

In three concluding reactions, product IX was freed of all protective groups. By hydrogenolysis in 2,2,2-trifluoroethanol with Pd/C, all of the benzyloxycarbonyl protective groups and the C-terminal benzyl ester could be removed (yield 96%). By 30 minutes of subjection to the action of a mixture of trifluoroacetic acid and dichloromethane in a ratio of 1:1 by volume, in the presence of 10% by volume of anisole, the tertiary butyl ester groups were mainly split off. After the volatile components had been removed in vacuo at room temperature, pure trifluoroacetic acid was added to the residue of polypeptide and anisole in order to split off the 4,4'-dimethoxybenzohydryl protective group and any remaining tertiary butyl residues (120 minutes at about 20° C.). After precipitation and washing with ether, the synthetic thymosin $\alpha_1$ was purified chromatographically. For this purpose a column (0.6×240 cm) containing Bio-Gel P6 was used to determine first the retained volume of the oxidized insulin-B chain (molecular weight 3495) in 1% acetic acid (containing 10% of trifluoroethanol), and then the synthetic thymosin $\alpha_1$ was chromatographed. It emerged from the column in the volume corresponding to its molecular weight (3107) (yield 90% with respect to fragment IX). Amino acid analysis: (calculated values between parentheses; 6 N HCl/110° C./24, 48, 96 hours): Asp 4.11 (4); Thr 2.86 (3), Ser 2.70 (3), Glu 5.89 (6), Lys 3.98 (4), Ile 0.97 (1), Leu 1.00 (1), Ala 3.05 (3), Val 2.97 (3). Thin layer chromatogram (Merck 60 F-254 silica gel, 0.25 mm). $R_f$=0.16 (n-butanol/pyridine/glacial acetic acid/water 5:5:1:4 (V/V), uniformly.

$[\alpha]_\lambda^{25}$: $-96°$ (579 nm).

$-201.7°$ (435 nm), $-242.5°$ (408 nm), $-338.5°$ (365 nm), $-587.0°$ (313 nm); c=0.083 in water.

The synthetic thymosin $\alpha_1$ proved to be biologically active in the test for lymphocyte stimulation, in the E-rosette test and in the mitogen test.

We claim:

1. Polypeptides of the sequence Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn, characterized in that at least one of the amino acids 10, 15, 21, 25 and/or 28 is present as amide or alkyl amide, and/or amino acid 1 bears an acyl group other than acetyl, having up to 6 carbon atoms, especially an acyl glycine residue.

2. Thymosin $\alpha_1$ fragment I of the formula

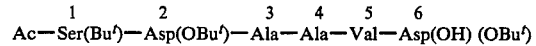

in which the fragment can bear, instead of the acetyl group, a different acyl group, especially an acyl glycine group, as well as the benzyl ester thereof.

3. Thymosin $\alpha_1$ fragment II of the formula

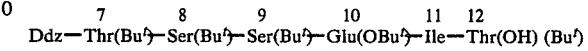

the glutamic acid residue 10 being able to be present as amide or alkyl amide, as well as the methyl ester thereof.

4. Thymosin $\alpha_1$ fragment III of the formula

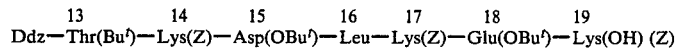

the aspartic acid residue 15 being able to be present as amide or alkyl amide, as well as the methyl ester thereof.

5. Thymosin $\alpha_1$ fragment IV of the formula

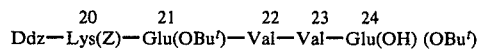

wherein the glutamic acid residue 21 can be present as amide or alkyl amide, as well as the methyl ester thereof.

6. Thymosin fragment V of the formula

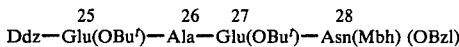

wherein the glutamic acid residue 25 can be present as amide or alkyl amide and the asparagine residue 28 can be present as diamide or dialkyl amide, as well as the benzyl ester thereof.

7. Thymosin fragment VI of the formula

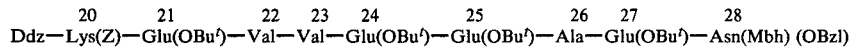

wherein the glutamic acid residues 21 and 25 and/or the asparagine residue 28 can be present as amide or alkyl amide, or as diamide or as dialkyl amide.

8. Thymosin fragment VII of the formula

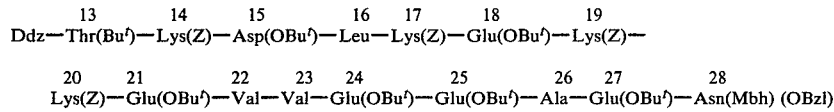

wherein the glutamic acid residues 21 and 25, the aspartic acid residue 15 and/or the asparagine residue 28 can be present as amide or alkyl amide, or as diamide or as dialkyl amide.

* * * * *